United States Patent [19]

Gee

[11] Patent Number: 5,300,286
[45] Date of Patent: Apr. 5, 1994

US005300286A

[54] SILICONE EMULSION FOR PERSONAL CARE APPLICATION

[75] Inventor: Ronald P. Gee, Midland, Mich.

[73] Assignee: Dow Corning Corporation, Midland, Mich.

[21] Appl. No.: 913,554

[22] Filed: Jul. 14, 1992

[51] Int. Cl.$^5$ .............................................. A61K 9/107
[52] U.S. Cl. ................................. 424/78.03; 514/865; 514/938; 514/975; 252/312; 252/DIG. 1
[58] Field of Search .................... 424/70, 486, 78.03; 514/865, 937, 938, 975; 252/DIG. 1, 312

[56] References Cited

U.S. PATENT DOCUMENTS

| | | | |
|---|---|---|---|
| 4,502,889 | 3/1985 | Kurita | 524/437 |
| 4,784,844 | 11/1988 | Thimineur et al. | 424/70 |
| 4,788,001 | 11/1988 | Narula | 514/941 |

*Primary Examiner*—Edward Webman
*Attorney, Agent, or Firm*—James L. DeCesare

[57] ABSTRACT

A silicone oil-in-water emulsion composition and a method of topically treating human skin with the composition. The emulsion constitutes water, a silicone oil, and at least two nonionic emulsifiers. Each nonionic emulsifier is a solid at room temperature. One nonionic emulsifier has an HLB value less than 8.0, while the other nonionic emulsifiers has an HLB value greater than 15.0.

7 Claims, No Drawings

SILICONE EMULSION FOR PERSONAL CARE APPLICATION

BACKGROUND OF THE INVENTION

This invention is directed to a silicone emulsion containing only certain nonionic surfactants. It has been found that such emulsions possess unexpected properties when applied in the field of personal care.

An emulsion is a disperse system consisting of two or more mutually insoluble or sparingly soluble liquids. One liquid is termed the continuous or external phase in which a second liquid is dispersed in the form of particles. The second liquid is termed the internal or dispersed phase. Emulsions are prepared by mechanically breaking up the internal phase. Typically, high-speed stirrers, propeller or turbine agitators, colloid mills, and homogenizers are employed. Emulsifiers or surfactants prevent droplets from reuniting once they are formed, and if the external phase consists of water and the internal phase is an organic liquid, an oil-in-water emulsion is produced. If water is finely dispersed in a nonaqueous liquid, the result is a water-in-oil emulsion.

In the majority of cases, emulsions are prepared with the aid of one or more emulsifiers each having a different HLB value. There are four categories of surface active emulsifiers namely nonionic, anionic, cationic, and ampholytic or amphoteric. In anionic surfactants, the surface active ion carries a negative charge. In cationic surfactants, the charge is positive. In nonionic surfactants, there is no charge on the molecule. In ampholytic and amphoteric surfactants, both positive and negative charges exist in the molecule.

In order to assist formulators in the selection of an emulsifier or surfactant system, a dimensionless number between 1–20 has been assigned to each emulsifier for the purpose of providing information on its water and oil solubility. Numbers between 0–9 characterize oil soluble lipophilic products, whereas numbers between 11–20 indicate water soluble hydrophilic compounds. Substances with a hydrophilic-lipophilic balance (HLB) value of 10 have about the same affinity for both oil and water, and are distributed between the two phases so that the hydrophilic group projects completely into the water while the lipophilic hydrocarbon group is adsorbed in the nonaqueous phase. Surfactants with an HLB value of eleven or more are known to stabilize emulsions against particle coalescence.

The color of an emulsion often reveals a rough indication of the particle size of the droplets in the internal phase. If the particles are macroglobules, two phases may be distinguished. If the particle size exceeds one micron, milky-white emulsions are formed. If the particle size falls within the range of 0.1–1.0 microns, emulsions exhibiting a blue-white hue are produced. Emulsions containing particles with a size in the range of 0.05–0.1 microns possess a gray semitransparent appearance. Transparent emulsions result where the particle size is 0.05 microns and less.

The contribution to the existing state of the emulsion art provided in accordance with the present invention resides in the unexpected discovery that the level of resistance of water penetration through a silicone oil residue deposited from an oil-in-water emulsion into a substrate may be increased by forming the oil-in-water silicone emulsion with the aid of two specific and particular types of nonionic surfactant. More particularly, there must be employed at least one nonionic surfactant having a lower HLB value less than 8.0, and preferably a nonionic surfactant which is a solid at room temperature having an HLB value less than 6.0. It is also possible to employ a fatty alcohol such as lauryl alcohol, myristyl alcohol, stearyl alcohol, behenyl alcohol, or cetyl alcohol, as the lower HLB value surfactant. The lower HLB value surfactant is used in combination with at least one nonionic surfactant having a higher HLB value greater than 15.0, and preferably a nonionic surfactant which is a solid at room temperature and which has an HLB value greater than 17.0. Excluded and otherwise considered to be inoperative nonionic surfactants in accordance with the concept of the present invention are liquid nonionic surfactants, and nonionic surfactants having a range of HLB values of 8.0–15.0.

The advantages provided by the present invention are realized by complying with the foregoing requirements of the surfactant package. Other anionic, cationic, ampholytic, or amphoteric surface active emulsifiers may be present in smaller amounts of less than about one percent by weight in those situations wherein the emulsion is prepared by emulsion polymerization in which an ionic surfactant is required as a constituent of the polymerization catalyst.

SUMMARY OF THE INVENTION

The invention relates to a silicone oil-in-water emulsion which contains water, a silicone oil, and only nonionic types of surfactants which are solids at room temperature, in which at least two distinct categories of nonionic surfactants are employed. One nonionic surfactant is required to possess an HLB value less than 8.0, and preferably less than 6.0; while the other nonionic surfactant is required to possess an HLB value greater than 15.0, and preferably greater than 17.0. Alternatively, a fatty alcohol such as lauryl alcohol, myristyl alcohol, or cetyl alcohol, may be substituted for the lower HLB value surfactant. In such case, it is required that the fatty alcohol be a solid at room temperature.

The invention further relates to the use of the above described silicone oil-in-water emulsions for personal care applications, in which the emulsion is applied to the skin for the purpose of alleviating one or more of the common dermatological skin disorders suffered by humans caused by an over-exposure to water, such as diaper rash.

These and other objects, features, and advantages of the herein described present invention will become apparent when considered in light of the following detailed description thereof.

DETAILED DESCRIPTION OF THE INVENTION

For purposes of the present invention, the first category of nonionic surfactant employed has an HLB value less than 8.0, preferably less than 6.0, and thus insoluble in water. Representative emulsifiers in this category which are all solids at room temperature are: (a) Brij 52 which is a polyoxyethylene cetyl ether and a product of ICI Americas Inc. of Wilmington, Del., having an HLB value of 4.9; (b) Brij 72 which is a polyoxyethylene stearyl ether and a product of ICI Americas Inc. of Wilmington, Del., having an HLB value of 4.9; (c) Arlacel 60 which is sorbitan stearate and a product of ICI Americas Inc. of Wilmington, Del., having an HLB value of 4.7; (d) Aldo MS which is glycerol monostearate and a product and trademark of Lonza Inc., of Fairlawn, N.J., having an HLB value of 3.9; (e) Aldo PGHMS which is propylene glycol monostearate and a product and trademark of Lonza Inc., of Fairlawn, N.J., having an HLB value of 3.0; (f) Mapeg EGMS which is ethylene glycol monostearate and a product and trademark of PPG/Mazer of Gurnee, Ill., having an HLB value of 2.9; (g) Hodag DGS which is diethylene glycol monostearate and a product of Hodag Chemical Corp., of Skokie, Ill., having an HLB value of 4.7; (h) Ethox SAM-2 which is a polyoxyethylene stearyl amine and a product of Ethox Chemicals, Inc., of Greenville, S.C., having an HLB value of 4.9; and (i) Macol SA-2 which is a polyoxyethylene stearyl ester and a product and trademark of PPG/Mazer of Gurnee, Ill., having an HBL value of 4.9. Fatty alcohols such as lauryl alcohol, myristyl alcohol, and cetyl alcohol, may be considered to be nonionic surfactants with an HLB value of about one, and hence could be included in this first category of nonionic surfactants.

The second category of nonionic surfactant employed in accordance with the concept of the present invention has an HLB value greater than 15.0, and preferably greater than 17.0. Representative emulsifiers in this second catergory of nonionic surfactant which are all solids at room temperature are: (i) Brij 700 which is a polyoxyethylene stearyl ether and a product of ICI Americas Inc. of Wilmington, Del., having an HLB value of 18.8; (ii) Mapeg S-40K which is a polyoxyethylene monostearate and a product and trademark of PPG/Mazer of Gurnee, Ill., having an HLB value of 17.2; (iii) Macol SA-40 which is steareth-40 and a product and trademark of PPG/Mazer of Gurnee, Ill., having an HLB value of 17.4; (iv) Triton X-405 which is octylphenoxy polyethoxy ethanol and a product and trademark of Union Carbide Chem. & Plastics Co., Industrial Chemicals Div., Danbury, Conn., having an HLB value of 17.9; (v) Macol SA-20 which is steareth-20 and a product and trademark of PPG/Mazer of Gurnee, Ill., having an HLB value of 15.4; and (vi) Tergitol 15-S-20 which is a C11-C15 secondary alcohol ethoxylate and a product and trademark of Union Carbide Chem. & Plastics Co., Industrial Chemicals Div., Danbury, Conn., having an HLB value of 16.3.

Each of the above particular surfactants are merely set forth herein for the purpose of identifying representative emulsifiers which may be employed in accordance with the precepts of the present invention. It should be understood that other equivalent nonionic emulsifier products which are solids at room temperature may also be substituted. Thus, it would be appropriate to use for example, (i) other alcohol ethoxylates which are solids at room temperature besides Brij 52, Brij 72, and Brij 700; (ii) other alkylphenol ethoxylates which are solids at room temperature besides Triton X-405; (iii) other glycerol esters of fatty acids which are solids at room temperature beside Aldo MS; and (iv) other glycol esters of fatty acids which are solids at room temperature besides Aldo PGHMS and Hodag DGS.

The solid form of representative ones of the aforementioned emulsifiers at room temperature can be seen by reference to the following list of their melting point or pour point which is the lowest temperature at which a liquid will flow when a test container is inverted.

| Emulsifier | Pour Point (degrees Centigrade) |
| --- | --- |
| Aldo MS | 58 |
| Aldo PGHMS | 40 |
| Arlacel 60 | 53 |
| Brij 52 | 33 |
| Brij 72 | 43 |
| Brij 700 | 55 |
| Macol SA-40 | 40 |
| Mapeg EGMS | 56 |
| Mapeg S-40K | 44 |
| Cetyl alcohol | 49 |
| Myristyl alcohol | 38 |
| Lauryl alcohol | 24 |
| Stearyl alcohol | 60 |
| Behenyl alcohol | 71 |

Room temperature for purposes of the present invention is considered to be an ambient temperature of from 20–23 degrees Centigrade.

The silicone oil component of the oil-in-water emulsions of the present invention constitutes organic polysiloxane liquids which have a viscosity in the range of 0.65 to as high as several million centristokes, preferably about one to about 10,000 centistokes, and most preferred about 5–2000 centistokes. A single viscosity silicone fluid or a mixture of polysiloxane fluids having relatively higher and relatively lower viscosities may be employed. Such polysiloxanes have the repeating unit

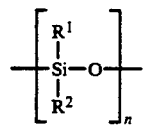

wherein n is an integer having a value greater than 1, $R^1$ and $R^2$ are each an alkyl radical containing 1 to 7 carbon atoms, inclusive, or a phenyl group. Illustrative polysiloxanes encompassed by the above formula are polydimethylsiloxane, polydiethylsiloxane, polymethylethylsiloxane, polymethylphenylsiloxane, and polydiphenylsiloxanes. Both linear and branched polysiloxanes and blends thereof may be employed.

In those instances where mixtures of silicone fluids are employed, one or more of the fluids is preferably a lower viscosity methylsilicone fluid. The methylsilicone fluid corresponds to the average unit formula $(CH_3)_a SiO_{(4-a/2)}$ wherein a is an integer having an average value of from two to three. The methylsilicone fluid contains siloxane units joined by Si-O-Si bonds. Representative units are $(CH_3)_3 SiO_{\frac{1}{2}}$, $(CH_3)_2 SiO_{2/2}$, $(CH_3) SiO_{3/2}$, and $SiO_{4/2}$. These units are present in such molar amounts so that there is an average of from about two to three methyl groups per silicon atom in the methylsilicone fluid, and the fluid has a viscosity of less than about one hundred centistokes measured at twenty-five degrees Centigrade. Preferably, the methylsilicone fluid contains dimethylsiloxane units and optionally trimethylsiloxane units. Such methylsilicone fluids have a viscosity of less than about ten centistokes such as cyclopolysiloxanes of the general formula $[(CH_3)_2 SiO]_x$ and linear siloxanes of the general formula $(CH_3)_3 SiO[(CH_3)_2 SiO]_y Si(CH_3)_3$ in which x is an integer having a value of from three to ten and y is an integer having a value of from zero to about four.

Of particular utility in accordance with the present invention are those methylsilicone fluids which are volatile cyclic silicone fluids and voltatile linear silicone fluids. By "volatile" is meant that the silicone fluid has a boiling point generally less than about two hundred-fifty degrees Centigrade. Specific examples of these volatile methylsilicone fluids are polydimethylcy- closiloxane and the linear silicone fluid hexamethyl- disiloxane. Such volatile fluids have viscosities gener- ally less than about ten centistokes measured at twenty-five degrees Centigrade, and most preferably have viscosities between about 0.65 to 5.0 centistokes.

The volatile cyclic silicones generally conform to the formula $(R_2SiO)_x$ in which R is an alkyl radical having from one to three carbon atoms or a phenyl group. Most typically the cyclic siloxanes have the formula $[(CH_3)_2SiO]_x$ in which x is an integer from three to ten. Some representative volatile cyclic siloxane compounds found to be especially useful in accordance with the present invention are the methylsilicone tetramer octa- methylcyclotetrasiloxane and the methylsilicone penta- mer decamethylcyclopentasiloxane. Mixtures of the tetramer and pentamer may also be employed. Such cyclic siloxanes have viscosities ranging from about 2.5 centistokes to about five centistokes. These materials are otherwise known as cyclomethicone which is the CTFA adopted name of The Cosmetics, Toiletries and Fragrance Association, Inc., Washington, D.C.

The most preferred volatile low viscosity linear me- thylsilicone fluid has the formula $R_3SiO(R_2SiO)_nSiR_3$ in which R is an alkyl radical having one to six carbon atoms and n is an integer of from two to nine. Most representative of this class of volatile linear methylsilox- ane fluid is hexamethyldisiloxane of the formula

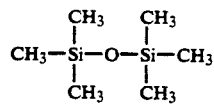

which has a viscosity of 0.65 centistokes measured at twenty-five degrees Centigrade.

Both the cyclic and linear low viscosity volatile me- thylsilicone materials are clear fluids and are essentially odorless, nontoxic, nongreasy and nonstinging. Cosmet- ically, these methylsilicone fluids are nonirritating to the skin and exhibit enhanced spreadability and ease of rub-out when applied to skin tissue. Once applied, these volatile silicone materials will evaporate leaving behind no residue. When employed in combination with a non- volatile silicone fluid, the non-volatile silicone fluid remains on the skin to provide the desired barrier to inhibit absorption of water and water soluble irritants into the skin. One particularly effective mixture in- cludes a high viscosity hydroxy-endblocked polyor- ganosiloxane, which may be used in combination with either a volatile cyclic silicone fluid or a lower viscosity non-volatile silicone fluid.

All of the aforementioned silicone oils and methods for their preparation are well known in the art, and such materials are commercially available. The terms "vola- tile" and "non-volatile" as applied to the silicone oils of the present invention are defined with respect to the boiling point of 250 degrees Centigrade. Thus, silicone oils having a boiling point less than 250 degrees are considered to be "volatile", whereas silicone oils having a boiling point in excess of 250 degrees are considered to be "non-volatile".

In mechanically prepared emulsions of mixtures of silicones, the mixture should include a non-volatile component having a viscosity generally in the range of 50-2,000 centistokes in combination with either a vola- tile linear silicone component or a volatile cyclic sili- cone component. In such instances, the volatile fluid reduces the viscosity of the mixture which aids in emul- sification to smaller particle size.

The emulsion contains from 1-70 percent by weight of the silicone oil or silicone oil mixture, 5-50 parts by weight of the lower HLB emulsifier per 100 parts of non-volatile silicone oil, 20-150 parts by weight of the higher HLB emulsifier per 100 parts of the lower HLB emulsifier, and the balance being water. Preferably, the emulsion contains about 55 percent by weight of the silicone oil or silicone oil mixture, and 10-30 parts by weight of the lower HLB emulsifier per 100 parts of non-volatile silicone oil.

The emulsions are prepared by one of two methods. One method is mechanical emulsification by mixing together water, the silicone oil, and the two nonionic surfactants, and passing the mixture through a high shear device such as a colloid mill or a homogenizer. A second method is by the emulsion polymerization of cyclic siloxanes in which there is formed simultaneously silicone polymers in emulsion form.

As is known in the art, emulsion polymerization typi- cally entails combining a reactive silicone oligomer, a surfactant, a polymerization catalyst, and water. The emulsion is stirred and the silicone oligomers are al- lowed to polymerize until a standard emulsion, a fine emulsion, or a microemulsion, is formed. Normally, alkoxysilanes which result in the formation of micro- emulsions or cyclic siloxanes, which in turn result in the formation of fine and standard emulsions, are used as the reactive monomers and oligomers. Combinations of the silicone reactants can also be used to form copoly- mers in the resulting emulsion. Such techniques are discussed in detail in European Patent Application 0 459 500 A2 published Dec. 4, 1991, entitled "Method of Making Polysiloxane Emulsions", which is assigned to the same assignee as the present invention.

The following examples are set forth for the purpose of further illustrating the present invention.

EXAMPLE I

The Collagen Film Test (CFT)

The unique nature of the silicone emulsion of the present invention was illustrated by a test for measuring the rate of water penetration into a sheet of collagen film which had been surface treated with the silicone emulsion and allowed to dry. The collagen film was used to simulate human skin. Untreated collagen film has a rate of water uptake of 0.58 grams of water by contact with wet filter paper for thirty minutes. This rate of water uptake was shown to have been signifi- cantly decreased upon treatment of the collagen film with the emulsion composition of the present invention. In the test, three circular sheets of collagen film were weighted and clamped into two plastic concentric rings with the film exposed for treatment. One ring had an inside diameter of 3.5 inches, while the other ring had an outside diameter of 3.5 inches. The film was treated with the emulsion by wiping the film with a KIMWIPE tissue dipped in a pre-diluted emulsion containing about 3.6 percent by weight of silicone content. The tissue was dipped in the emulsion, folded in half, and typically each of the four portions of the tissue were wiped three rotations across the film. The amount deposited can be varied by the amount of wiping. The film was allowed to dry for 10–15 minutes. The three sheets of collagen film were re-weighed in order to determine the weight of the material deposited on the film. One sheet of Whatman No. 4 filter paper was placed in a large petri dish. One gram of water was added, the dish was covered, and the water was allowed to soak the paper uniformly. The set of treated collagen films was placed face down on the filter paper, and a small petri dish was placed on top of the treated film as a weight. The large petri dish was covered and placed in a constant humidity chamber at about eighty-two percent humidity. At intervals of 2, 5, 10, 15, 20, and 30 minutes, the assembly was removed from the chamber and the collagen film was re-weighted. Each time the assembly was promptly returned to the chamber. The increase in weight of the collagen film was determined as a function of time. The weight increases after thirty minutes is set forth in the examples and tables set forth below.

EXAMPLE II

The Collagen Film Test in Example I was repeated using a collagen film treated with an emulsion not according to the present invention. The components of the emulsion are shown below, followed by the results of the CFT. The emulsion was pre-diluted to a silicone content of 3.6 percent by weight for the test.

TABLE I

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Brij 30 Emulsifier | 3.5 | 9.7 liquid |
| Tween 20 Emulsifier | 3.5 | 16.7 liquid |
| Water | 43.0 | — |
| Collagen Film Test: (grams of water at 30 min. per grams of material deposited) | 0.52 gm H$_2$O/0.009 gm deposit 0.52 gm H$_2$O/0.024 gm deposit 0.49 gm H$_2$O/0.048 gm deposit | |

Each emulsifier in Example II was present in an amount of 10.8 parts per one hundred parts of non-volatile silicone fluid.

EXAMPLE III

Example II was repeated with a collagen film treated with an another emulsion not according to the present invention. The components of the emulsion are shown below, followed by the results of the collagen film test. In this example, one surfactant was in accordance with the present invention and one was not.

TABLE II

| Emulsion ComPosition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Brij 30 Emulsifier | 3.5 | 9.7 liquid |
| Macol SA-40 Emulsifier | 3.5 | 17.4 solid |
| Water | 43.0 | — |
| Collagen Film Test: (grams of water at 30 min. per grams of material deposited) | 0.54 gm H$_2$O/0.021 gm deposit | |

As can be seen, there was no significant reduction in the water uptake by the collagen film.

EXAMPLE IV

Example III was repeated with a collagen film treated with an emulsion which was according to the present invention. The components of the emulsion are shown below, followed by the results of the collagen film test. In this example, both surfactants were in accordance with the present invention.

TABLE III

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Brij 72 Emulsifier | 3.5 | 4.9 solid |
| Macol SA-40 Emulsifier | 3.5 | 17.4 solid |
| Water | 43.0 | — |
| Collagen Film Test: (grams of water at 30 min. per grams of material deposited) | 0.47 gm H$_2$O/0.024 gm deposit 0.43 gm H$_2$O/0.032 gm deposit | |

By comparing the results of the collagen film tests in Tables I–III, it will be apparent that the emulsions in accordance with the present invention significantly reduce the amount of water taken up by the collagen film.

EXAMPLE V

In order to illustrate the effect of using various surfactants on the "barrier" performance of a silicone oil mixture in the Collagen Film Test, a series of Collagen Film Tests were conducted on simple blends of individual surfactants with the silicone oil. The influence of the individual surfactant HLB value and the physical state of the individual surfactant is apparent in Table IV. Table IV indicates that individual surfactants having an HLB value of less than about nine have a beneficial effect on the Collagen Film Test, except liquid surfactants such as Brij 92 which are detrimental.

In each test, there was employed 3.5 grams of an individual surfactant, 15.0 grams of a 1000 centistoke polydimethylsiloxane fluid, 17.5 grams of a 50.0 centistoke polydimethylsiloxane fluid, 17.5 grams of a volatile cyclic siloxane, and 46.5 grams of water. Each individual surfactant was present in an amount of 10.8 grams per 100 grams of non-volatile silicone component. Table IV reflects the individual surfactants employed, the grams of test solution deposited, the individual surfactant HLB and its form whether liquid or solid.

TABLE IV

| Surfactant | Grams Deposited | Grams of Water Absorbed on Film 30 Minutes | Form | HLB |
|---|---|---|---|---|
| None | 0.030 | 0.45 | — | — |
| Brij 92 | 0.025 | 0.54 | Liquid | 4.9 |
| Brij 30 | 0.025 | 0.58 | Liquid | 9.7 |
| Macol SA-2 | 0.026 | 0.35 | Solid | 4.9 |
| Macol SA-5 | 0.026 | 0.46 | Solid | 9.0 |
| Macol SA-10 | 0.026 | 0.50 | Solid | 12.3 |
| Macol SA-15 | 0.037 | 0.49 | Solid | 14.3 |
| Macol SA-20 | 0.023 | 0.50 | Solid | 15.4 |
| Macol SA-40 | 0.030 | 0.50 | Solid | 17.4 |

EXAMPLE VI

Example II was repeated with a collagen film treated with an other emulsion not according to the present invention. The components of the emulsion are shown below, followed by the results of the collagen film test. In this example, only one surfactant was used and was a surfactant having the lowest HLB value that would stabilize the emulsion.

TABLE V

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Macol SA-5 Emulsifier | 3.5 | 9.0 Solid |
| Water | 46.5 | — |
| Collagen Film Test: (grams of water at 30 min. per grams of material deposited) | 0.52 gm H₂O/0.020 gm deposit | |

As can be seen, the reduction in the water uptake by the collagen film was not as much as the silicone oil without a surfactant in Table IV, indicating a slight negative effect by the individual Macol SA-5 emulsifier.

EXAMPLE VII

Example II was repeated with a series of collagen films treated with several emulsions which were according to the present invention. The components of the emulsion are shown below, followed by the results of the collagen film test. In these examples, both surfactants were in accordance with the present invention.

TABLE VI

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Brij 72 Emulsifier | 3.5 | 4.9 solid |
| Macol SA-100 Emulsifier | 2.8 | 17.4 solid |
| Water | 43.7 | — |
| Collagen Film Test: (grams of water at 30 min. per grams of material deposited) | 0.47 gm H₂O/0.020 gm deposit | |

It should be apparent that this emulsion in accordance with the present invention significantly reduced the amount of water taken up by the collagen film.

TABLE VII

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Brij 52 Emulsifier | 3.5 | 5.3 solid |
| Macol SA-40 Emulsifier | 3.5 | 17.4 solid |
| Water | 43.0 | — |
| Collagen Film Test: (grams of water at 30 min per grams of material deposited) | 0.49 gm H₂O/0.018 gm deposit  0.44 gm H₂O/0.032 gm deposit  0.43 gm H₂O/0.058 gm deposit | |

It should be apparent that this emulsion in accordance with the present invention significantly reduced the amount of water taken up by the collagen film.

In Table VIII shown below, the Brij 72 emulsifier was employed in an amount of 12.3 parts per 100 parts of non-volatile silicone, and the Macol SA-40 emulsifier was present in an amount of 9.2 parts per 100 parts of non-volatile silicone.

TABLE VIII

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Brij 72 Emulsifier | 4.0 | 4.9 solid |
| Macol SA-40 Emulsifier | 3.0 | 17.4 solid |
| Water | 43.0 | — |
| Collagen Film Test: (grams of water at 30 min. per grams of material deposited) | 0.48 gm H₂O/0.026 gm deposit | |

It should be apparent that this emulsion in accordance with the present invention significantly reduced the amount of water taken up by the collagen film.

TABLE IX

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Volatile cyclic Silicone Fluid 5.0 centistokes | 17.5 | — |
| Lauryl Alcohol | 2.5 | — |
| Macol SA-40 Emulsifier | 3.5 | 17.4 solid |

TABLE IX-continued

| Emulsion Composition | Percent by Weight | HLB Value and Form |
|---|---|---|
| Water | 43.0 | — |
| Germaben IIE | 1.0 | — |
| Collagen Film Test: (grams of water at 30 min. per grams of material deposited) | 0.39 gm H$_2$O/0.006 gm deposit | |

It should be apparent that this emulsion in accordance with the present invention significantly reduced the amount of water taken up by the collagen film. In Table IX, lauryl alcohol was substituted for the lower HLB surfactant Brij 72 in Table VIII.

In Table X below, the three components of the silicone oil mixture were all non-volatile silicones. Accordingly, the Brij 72 emulsifier and the Macol SA-40 emulsifier were each employed in an amount of 7.0 parts per 100 parts of non-volatile silicone.

TABLE X

| Emulsion Composition | Percent by Weight | HLB Value and Form |
|---|---|---|
| Silicone fluid 1000 centistokes | 15.0 | — |
| Silicone fluid 50 centistokes | 17.5 | — |
| Silicone Fluid 10.0 centistokes | 17.5 | — |
| Brij 72 Emulsifier | 3.5 | 4.9 solid |
| Macol SA-40 Emulsifier | 3.5 | 17.4 solid |
| Water | 43.0 | — |
| Collagen Film Test: (grams of water at 30 min. per grams of material deposited) | 0.49 gm H$_2$O/0.054 gm deposit | |

It should be apparent that this emulsion in accordance with the present invention significantly reduced the amount of water taken up by the collagen film.

In Table XI below, the Brij 72 emulsifier and the Macol SA-40 emulsifier were each employed in an amount of 7.0 parts per 100 parts of the single non-volatile silicone.

TABLE XI

| Emulsion Composition | Percent by Weight | HLB Value and Form |
|---|---|---|
| Silicone fluid 1000 centistokes | 40.0 | — |
| Brij 72 Emulsifier | 2.8 | 4.9 solid |
| Macol SA-40 Emulsifier | 2.8 | 17.4 solid |
| Water | 45.4 | — |
| Germaben IIE | 1.0 | — |
| Collagen Film Test: (grams of water at 30 min. per grams of material deposited) | 0.50 gm H$_2$O/0.054 gm deposit | |

In the emulsion prepared according to Tables IX and XI, there was included a preservative Germaben IIE which is diazolidinyl urea and parabens. Germaben IIE is a product and a trademark of Sutton Laboratories Inc., Chatham, N.J.

It should be noted that while the emulsion of Table X reduced the amount of water taken up by the collagen film, the reduction was not as significant as some of the previous emulsions of the present invention which contained a mixture of non-volatile and volatile silicone fluids. Thus, the emulsion of Table XI contained less of the Brij 72 emulsifier per 100 parts of non-volatile silicone which is needed to offset the effect of the Macol SA-40 emulsifier.

The following example illustrates the invention as it pertains to an emulsion in accordance with the present invention which was prepared by emulsion polymerization techniques in contrast to the mechanical preparation thereof.

EXAMPLE VIII 259.70 grams of water, 21.0 grams of Tergitol 15-S-20, 17.5 grams of Arquad T27W, 24.5 grams of Brij 72, 245 grams of cyclic siloxanes having an average of four silicon atoms per molecule, and 2.1 grams of hexamethyldisiloxane, were added with stirring to a reaction flask and heated to eighty-five degrees Centigrade. To the mixture in the flask was added 2.8 grams of a fifty percent by weight solution of sodium hydroxide. The reaction was allowed to proceed for six hours with stirring before being neutralized with 2.1 grams of glacial acetic acid. This was followed by the addition to the flask of 125.0 grams of water and 0.21 grams of a commercial biocide. The resulting product was an oil-free emulsion having a particle size of silicone in the emulsion of 135 nanometers. The Collagen Film Test in Example I was repeated using collagen film treated with this emulsion. The emulsion was pre-diluted to a silicone content of 3.6 percent by weight for the test. The test results indicated that 0.42 grams of water were deposited on the film after thirty minutes at a deposit level of 0.043 grams. In comparison to Tables I and II, it should be apparent that the water uptake was reduced to a significant extent.

The foregoing examples and tables show the effectiveness of the emulsions of the present invention in their capability to decrease the penetration of water into a substrate which has been pre-treated with the emulsion and allowed to dry. This characteristic property and advantage renders these emulsions particularly suitable for topical skin care applications wherein the emulsion is rubbed gently into the skin and the deposited silicone film functions as a barrier to the influx of moisture and water into the skin. This property helps to reduce and ameliorate the severity of skin disorders and rashes for example caused by over-exposure to water, as in diaper rashes. In such applications, the emulsion may be formulated to include a perfume, a coloring agent, a preservative, and other adjuvants for rendering personal care products more aesthetically pleasing to the consumer.

For purposes of the present invention, a "standard" emulsion is defined as an emulsion having silicone particles of a particle diameter in excess of about three hundred nanometers. A "fine" emulsion is defined as an emulsion having silicone particles of a particle diameter of between about 140–300 nanometers. A "microemulsion" is defined as an emulsion having silicone particles of a particle diameter of less than about 140 nanometers. Particle size is determined using a particle size instrument operating on the principle of "quasi-elastic" light scattering in accordance with the cumulant method described in the "Journal of Chemistry & Physics", D. E. Koppal, Vol. 57, Page 4814, (1972).

In Table XII set forth below, there is depicted the particle size of emulsions prepared in accordance with various of the preceeding examples and Tables. Where applicable, the viscosity of the silicone fluid mixture or the single silicone fluid used to prepare the emulsion is set forth. In addition, the type of emulsion in each instance is identified.

TABLE XII

| Table/Example | Emulsion Type | Particle Size Nanometers | Viscosity Centipoise |
|---|---|---|---|
| Table I | Fine | 271 | 76 |
| Table II | Standard | 355 | — |
| Table III | Standard | 408 | — |
| Table VI | Standard | 586 | — |
| Table VII | Standard | 413 | — |
| Table VII | Standard | 393 | — |
| Table X | Standard | 443 | 81 |
| Table XI | Standard | 1181 | 1000 |
| Example VIII | Microemulsion | 135 | — |

While the standard emulsions shown in Table XII are useful for purposes of the present invention, the preferred emulsion types are the fine emulsion and the microemulsion. Thus, while emulsions having a particle size in excess of about three hundred nanometers are suitable, the preferred emulsions have a particle size of between about 140-300 nanometers, most preferably less than about 140 nanometers.

It should also be apparent from a consideration of Table XII, that emulsions having much smaller particle size result where the silicone fluid or the mixture of silicone fluids used to prepare the emulsion have a low viscosity. Thus, in Table XII, the standard emulsion resulting from use of a single silicone fluid of 1000 centipoise had a particle size of 1181 nanometers, in comparision to the emulsions made from silicone fluid mixtures having an overall viscosity of less than about one hundred centipoise (specifically 78-81 centipoise) which had a particle size much less than 1181 nanometers.

As with any over-the-counter skin treating product, use of the emulsion of the present invention is simply a matter of placing a small amount of the emulsion in the palm of one hand, rubbing the hands together, and using the hands to gently rub the emulsion on the areas of the body to coat the skin. Repeated daily topical applications may be required.

It will be apparent from the foregoing that many other variations and modifications may be made in the compounds, compositions, structures, and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A silicone oil-in-water emulsion composition comprising 1-70 percent by weight of a mixture of a plurality of silicone oils, and at least two nonionic emulsifiers, each nonionic emulsifier being a solid at room temperature, one of said nonionic emulsifiers having a lower HLB value less than 6.0, the lower HLB value emulsifier being present in the amount of 5-50 parts by weight per 100 parts of silicone oils in the mixture, and the other of said nonionic emulsifiers having a higher HLB value greater than 17.0, the higher HLB value emulsifier being present in the amount of 20-150 parts by weight per 100 parts of the lower HLB value emulsifier, the balance of the composition being water, the particle size of the silicone oils in the emulsion being between 140-300 nanometers, all of the silicone oils in the emulsion being non-volatile silicones having a viscosity between 50-2000 centistokes.

2. A composition according to claim 1 in which there is included as one of the emulsifiers a fatty alcohol which is a solid at room temperature and which is selected from the group consisting of lauryl alcohol, myristyl alcohol, stearyl alcohol, behenyl alcohol, and cetyl alcohol.

3. A composition according to claim 1 in which there are at least three non-volatile silicone oils in the silicone oil mixture, one of the silicone oils having a viscosity of at least fifty centistokes, and another of the silicone oils having a viscosity of at least one thousand centistokes.

4. A silicone oil-in-water emulsion composition comprising 1-70 percent by weight of a mixture of a plurality of silicone oils, and at least two nonionic emulsifiers, each nonionic emulsifier being a solid at room temperature, one of said nonionic emulsifiers having a lower HLB value less than 6.0, the lower HLB value emulsifier being present in the amount of 5-50 parts by weight per 100 parts of silicone oils in the mixture, and the other of said nonionic emulsifiers having a higher HLB value greater than 17.0, the higher HLB value emulsifier being present in the amount of 20-150 parts by weight per 100 parts of the lower HLB value emulsifier, the balance of the composition being water, the particle size of the silicone oils in the emulsion being between 140-300 nanometers, all of the silicone oils in the emulsion being non-volatile silicones having a viscosity between 50-2000 centistokes, there being at least three non-volatile silicone oils in the emulsion, one of the silicone oils having a viscosity of at least fifty centistokes, and another of the silicone oils having a viscosity of at least one thousand centistokes.

5. A method of establishing a barrier on human skin to decrease the penetration of water into the skin comprising topically applying to the skin a silicone oil-in-water emulsion and allowing the emulsion to dry, the emulsion including 1-70 percent by weight of a mixture of a plurality of silicone oils, and at least two nonionic emulsifiers, each nonionic emulsifier being a solid at room temperature, one of said nonionic emulsifiers having a lower HLB value less than 6.0, the lower HLB value emulsifier being present in the amount of 5-50 parts by weight per 100 parts of silicone oils in the mixture, and the other of said nonionic emulsifiers having a higher HLB value greater than 17.0, the higher HLB value emulsifier being present in the amount of 20-150 parts by weight per 100 parts of the lower HLB value emulsifier, the balance of the emulsion being water, the particle size of the silicone oils in the emulsion being between 140-300 nanometers, all of the silicone oils in the emulsion being non-volatile silicones having a viscosity between 50-2000 centistokes.

6. A method according to claim 5 in which there is included as one of the emulsifiers a fatty alcohol which is a solid at room temperature and which is selected from the group consisting of lauryl alcohol, myristyl alcohol, stearyl alcohol, behenyl alcohol, and cetyl alcohol.

7. A method according to claim 5 in which there are at least three non-volatile silicone oils in the silicone oil mixture, one of the silicone oils having a viscosity of at least fifty centistokes, and another of the silicone oils having a viscosity of at least one thousand centistokes.

* * * * *